United States Patent [19]

Cells

[11] Patent Number: 5,461,172
[45] Date of Patent: Oct. 24, 1995

[54] LIGHT-COLORED MANGANESE CARBOXYLATES

[75] Inventor: Paul L. Cells, Cleveland, Ohio

[73] Assignee: Mooney Chemicals, Inc., Cleveland, Ohio

[21] Appl. No.: 103,963

[22] Filed: Aug. 9, 1993

[51] Int. Cl.⁶ .................................................. C07F 13/00
[52] U.S. Cl. .................... 556/49; 106/287.18; 252/35; 44/363
[58] Field of Search ................................................ 556/49

[56] References Cited

U.S. PATENT DOCUMENTS

| | | | |
|---|---|---|---|
| 2,584,041 | 1/1952 | Nowak et al. | 260/414 |
| 3,762,890 | 10/1973 | Collins | 44/66 |
| 4,162,986 | 7/1979 | Alkaitis et al. | 252/33.2 |
| 4,633,001 | 12/1986 | Cells | 556/44 |
| 4,783,221 | 11/1988 | Grove | 106/18.22 |
| 4,786,326 | 11/1988 | Grove | 106/15.05 |
| 4,824,611 | 4/1989 | Cells | 260/414 |

FOREIGN PATENT DOCUMENTS 0188116  7/1986  European Pat. Off. .

*Primary Examiner*—Porfirio Nazario-Gonzales
*Attorney, Agent, or Firm*—Renner, Otto, Boisselle & Sklar

[57] ABSTRACT

This invention relates to light-colored manganese carboxylates and to a process for preparing manganese carboxylates. The manganese carboxylate salts are derived from (a) at least one carboxylic acid containing at least about six carbon atoms and characterized by the Formula (I)

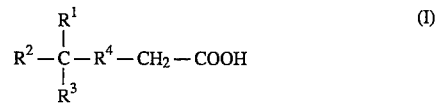

wherein $R^1$, $R^2$ and $R^3$ are each independently hydrogen or alkyl groups, and $R^4$ is an aliphatic hydrocarbylene group or (b) a carboxylic acid mixture comprising at least one carboxylic acid containing at least about six carbon atoms wherein at least about 75% by weight of the carboxylic acids containing at least six carbon atoms in the mixture are characterized by Formula I. Hydrocarbon solutions of such manganese carboxylates are lighter in color and more color stable than hydrocarbon solutions of similar manganese carboxylates wherein the carbon atom alpha to the carboxyl group contains one or two substituents.

23 Claims, No Drawings

LIGHT-COLORED MANGANESE CARBOXYLATES

TECHNICAL FIELD

The present invention relates to novel manganese salts of organic carboxylic acids. The invention also relates to a method for preparing manganese salts of organic carboxylic acids.

Metal salt compositions, including transition metal salt compositions have been described in the prior art as being useful in a variety of applications including: siccatives for paints, varnishes and inks; stabilizers in diverse plastics; curing agents in polyesters; additives for grease and lubricating oils; additives for fuels and fuel oils; and additives in wood preservatives.

It is well known that metal soaps serve in a wide variety of specific industrial uses to catalyze the transformation of drying oils into solid condition by promoting the mechanism of oxidation, polymerization and association. Lead, cobalt, manganese and calcium soaps are among those commonly employed for this purpose.

Many types and mixtures of metal salts and soaps of natural or synthetic organic acids, particularly carboxylic acids, have been suggested and commercially offered for several decades. One of the advantages of metal salts and soaps of carboxylic acids is that they provide a source of metals in forms which are soluble in organic liquids, especially in various hydrocarbon oils and solvents, to form solutions having various desired properties and uses. The desire for economy in the production of such materials or for improved product quality has led to a number of variations and methods of producing the metal soap compounds. Moreover, as various organic carboxylic acids have become available in commercial quantities, either from new natural sources, or as synthetic acids or standardized synthetic acid mixtures, the possibility of using these acids to produce metallic salts or soaps has been motivated, for example, by a lower price; by a relative uniformity of the commercial acids; by better color; or at times the non-colored characteristics of the salt products; by higher solubility of the salt products and various solvents; or improved stability in storage of the metal compositions or of their solutions.

U.S. Pat. No. 3,762,890 (Collins) describes hydrocarbon solutions of hydrolyzable manganese soaps. The solutions contain, in addition to a manganese fatty acid soap containing more than 4 carbon atoms, propionic acid in an amount effective to stabilize a liquid composition against emulsion with water. There is a reference to manganese branched chain carboxylates in Col. 1, lines 26–27, and an example of a specific branched chain carboxylate found in the patent is manganese neodecanoate.

The preparation of transition metal salts of organic carboxylic acids is described in U.S. Pat. Nos. 4,633,001 (Cells) and 4,824,611 (Cells). In general, the inventions described in these patents relate to processes for preparing transition metal salts from transition metals which are capable of having a multiplicity of oxidation states. In the process, the first step comprises providing a transition metal compound (preferably an oxide) wherein the transition metal is at one of its higher positive oxidation states. The transition metal is one from the first transitional series, and manganese is one of the elements mentioned in the two patents. The process described and claimed in U.S. Pat. No. 4,824,611 involves treating said transition metal compound with at least one inorganic reducing agent forming an intermediate contained in the transition metal and a lower positive oxidation state, and reacting said intermediate with at least one organic carboxylic acid containing at least five carbon atoms to form the desired metal salt. Examples of the reducing agents include metal bisulfites such as sodium bisulfite and various hydrazine sources such as hydrazine, hydrazine hydrate and solutions of hydrazine in water. The organic carboxylic acids utilized in the process are preferably aliphatic or alicyclic monocarboxylic acids, and mixtures of two or more monocarboxylic acids can be utilized. A number of monocarboxylic acids are listed in Col. 4, lines 33–44, and these include, hexoic acid, 2-ethylhexoic acid, isooctanoic acid, isononanoic acid, commercially available standardized nonanoic acid, decanoic acid, etc. Examples of useful mixtures which are illustrated include mixtures of propionic and 2-ethylhexanoic acid; oxalic acid and 2-ethylhexanoic acid; etc.

The procedure described in U.S. Pat. No. 4,633,001 is generally similar to the procedure described in the '611 patent with an additional step added to the process which involves mixing the transition metal salt formed in a process similar to the process described in the '611 patent with either at least one antioxidant or at least one additional metal salt wherein the additional metal is more electronegative than the transition metal salt, or mixtures of the antioxidant and the additional metal salt. The general discussion of useful transition metals and the listing of suitable monocarboxylic acids in the '001 patent is similar to the disclosures found in the '611 patent.

U.S. Pat. No. 4,162,986 (Alkaitis et al) describes highly overbased oil-soluble high metal content transition metal organic oxy, hydroxy, complexes. The complexes are prepared by reacting a transition metal source with mixed organic acids comprising at least one monocarboxylic acid and a second acid, either a sulfonic acid or a different molecular weight carboxylic acid. The organic monocarboxylic acids identified in the patent include propionic acid, butyric acid, 2-ethylhexanoic acid, commercially available standarized nonanoic acid, neodecanoic acid, oleic acid, etc.

U.S. Pat. Nos. 4,783,221 (Grove) and 4,786,326 (Grove) describe compositions useful for preserving wood which comprise at least one metal salt of a carboxylic acid containing at least 6 carbon atoms wherein the metal is a transition metal, zinc, mercury, antimony or lead. In the '326 patent the compositions also contain at least one isothiazolone. A number of carboxylic acids are disclosed in the two patents including 2-ethylhexanoic acid, isooctanoic acid, isononanoic acid and neodecanoic acid.

SUMMARY OF THE DISCLOSURE

This invention relates to light-colored manganese carboxylates and to a process for preparing manganese carboxylates. The manganese carboxylate salts are derived from (a) at least one carboxylic acid containing at least about six carbon atoms and characterized by the Formula (I)

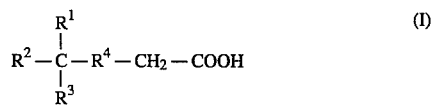

wherein $R^1$, $R^2$ and $R^3$ are each independently hydrogen or alkyl groups, and $R^4$ is an aliphatic hydrocarbylene group or (b) a carboxylic acid mixture comprising at least one carboxylic acid containing at least about six carbon atoms wherein at least about 75% by weight of the carboxylic acids containing at least six carbon atoms in the mixture are characterized by Formula I. Hydrocarbon solutions of such manganese carboxylates are lighter in color and more color stable than hydrocarbon solutions of similar manganese carboxylates wherein the carbon atom alpha to the carboxyl group contains one or two substituents.

DESCRIPTION OF THE PREFERRED EMBODIMENTS

In general, the present invention relates to manganese carboxylate salts of certain carboxylic acids and to a method of preparing such carboxylate salts. In one embodiment, the manganese carboxylate salts of the invention may be derived from (a) at least one carboxylic acid containing at least about 6 carbon atoms being characterized by the Formula I

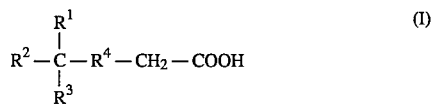

wherein $R^1$, $R^2$ and $R^3$ are each independently hydrogen or alkyl groups, and $R^4$ is an aliphatic hydrocarbylene group. Generally, the carboxylic acid (I) will contain from about 6 to about 30 carbon atoms and more often from about 6 to about 15 carbon atoms. In one embodiment, $R^1$, $R^2$ and $R^3$ are each independently hydrogen or alkyl groups containing from 1 to about 4 carbon atoms, and in another embodiment, $R^1$ and $R^2$ are alkyl groups containing from 1 to about 4 carbon atoms, and $R^3$ is either hydrogen or an alkyl group containing 1 to about 4 carbon atoms. The hydrocarbylene group $R^4$ is a divalent aliphatic group containing from 1 to about 25 carbon atoms and more often from about 1 to about 10 carbon atoms. The hydrocarbylene group $R^4$ may be a straight chain or a branched chain group.

Specific examples of carboxylic acids characterized by Formula I include: 4-methylpentanoic acid, 5-methylhexanoic acid, 3-ethylhexanoic acid, 3,5-dimethylhexanoic acid, 4,5-dimethylhexanoic acid, 3,4-dimethylhexanoic acid, 3,5,5-trimethylhexanoic acid, 4-methylheptanoic acid, 5-methylheptanoic acid, 6-methylheptanoic acid, 4,6-dimethylheptanoic acid, 7-methyloctanoic acid, 8-methylnonanoic acid, 9-methyldecanoic acid, and 11-methyldodecanoic acid. Presently preferred examples of acids within Formula I are those wherein $R^1$ and $R^2$ are each independently alkyl groups containing 1 to 4 carbon atoms, more preferably methyl groups, and $R^3$ is hydrogen or an alkyl group containing 1 to 4 carbon atoms, and more preferably, hydrogen or a methyl group. Examples of such preferred acids include 4-methylpentanoic acid; 5-methylhexanoic acid; 3,5-dimethylhexanoic acid; 5,5-dimethylhexanoic acid and 3,5,5-trimethylhexanoic acid.

Mixtures of such acids of Formula I can be utilized to prepare the manganese carboxylate salts of the present invention. For example, the mixture of acids of Formula I may contain at least about 40% by weight of "iso" carboxylic acids of Formula I wherein $R^1$ and $R^2$ are methyl groups and $R^3$ is hydrogen or a methyl group, and the remaining acids are characterized by Formula I but are different acids, e.g., not "iso" acids. Thus, in such mixtures (a), all of the carboxylic acids present in the mixture are characterized by Formula I.

The manganese carboxylate salts of the present invention also may be derived from mixtures of carboxylic acids wherein one or more of the carboxylic acids are not characterized by Formula I. Such carboxylic acid mixtures (b) comprise at least one carboxylic acid containing at least about 6 carbon atoms, and at least about 75%, 80% or even 85% by weight of the carboxylic acids containing at least 6 carbon atoms in the mixture are characterized by Formula I. Such carboxylic acid mixtures may contain carboxylic acids containing less than 6 carbon atoms such as acetic acid, propionic acid, butyric acid or pentanoic acid in addition to a carboxylic acid of Formula I. The carboxylic acid mixture (b) also may contain one or more carboxylic acids containing 6 or more carbon atoms which are not characterized by Formula I provided that at least about 75% by weight of the carboxylic acids containing at least 6 carbon atoms in the mixture are characterized by Formula I. Examples of carboxylic acids containing at least about 6 carbon atoms which are not characterized by Formula I include carboxylic acids wherein the alpha or 2-position is substituted, and such carboxylic acids are exemplified by 2-methylhexanoic acid, 2-ethylhexanoic acid, 2,4-dimethylhexanoic acid, 2,2-dimethyloctanoic acid (neodecanoic acid) and 2-methyloctanoic acid.

The carboxylic acid mixtures of (b) may comprise mixtures of (i) carboxylic acids containing at least 6 carbon atoms wherein at least about 75% by weight of the carboxylic acids containing at least 6 carbon atoms are characterized by Formula I, and (ii) at least one aliphatic carboxylic acid containing from 1 to 4 carbon atoms such as formic acid, acetic acid, propionic acid and butyric acid. For example, the manganese salt may be derived from a carboxylic acid mixture comprising (i) from about 75% to about 95% by weight of a mixture of carboxylic acids containing at least 6 carbon atoms wherein at least about 75%, 80% or even 85% by weight of the carboxylic acids containing at least about 6 carbon atoms in the mixture are characterized by Formula I, and (ii) from about 5% to about 25% by weight of at least one carboxylic acid containing from 1 to 5 carbon atoms. Preferably, the carboxylic acid contains from 2 to 4 carbon atoms and more preferably is propionic acid.

There are commercially available mixtures of carboxylic acids which contain one or more acids of Formula I and one or more carboxylic acids containing 6 or more carbon atoms which are not characterized by Formula I. Such mixtures in which at least about 75% or 80% or even 85% of the acids containing 6 or more carbon atoms are characterized by Formula I are useful in this invention. One example of such commercially available carboxylic acid mixtures is Cekanoic C8 acid, (Isooctanoic Acid) available from Exxon. Cekanoic C8 acid comprises a mixture of isomers of octanoic acid wherein about 88% of the acids are characterized by Formula I. Among the acids of Formula I in Cekanoic C8 acid are: 3,5-dimethylhexanonic acid; 4,5-dimethylhexanoic acid; 1,4-methylheptanoic acid; 3,4-dimethylhexanoic acid; 3-ethylhexanoic acid; 6-methylheptanoic acid; and 5-methylheptanoic acid. Another example of a commercial mixture available from Exxon is "Isononanoic Acid" which is reported to comprise about 97% of 3,5,5-trimethylhexanoic acid.

Specific examples of carboxylic acid mixtures (b) from which the manganese carboxylate salts of the present invention may be derived include the following mixtures wherein the percentages are by weight.

| Mixture 1. | |
|---|---|
| 3,5-dimethylhexanoic acid | 80% |
| 2-ethylhexanoic acid | 20% |

-continued

| Mixture 2. | |
|---|---|
| 3,5-dimethylhexanoic acid | 65% |
| 3,5,5-trimethylhexanoic acid | 20% |
| 2,4-dimethylhexanoic acid | 10% |
| 2-ethylhexanoic acid | 5% |
| Mixture 3. | |
| 3,5-dimethylhexanoic acid | 65% |
| 4,5-dimethylhexanoic acid | 10% |
| propionic acid | 25% |
| Mixture 4. | |
| 4,5-dimethylhexanoic acid | 60% |
| 5-methylheptanoic acid | 20% |
| 2,4-dimethylhexanoic acid | 10% |
| propionic acid | 10% |
| Mixture 5. | |
| Cekanoic C8 acid (Exxon) | 100% |
| Mixture 6. | |
| Cekanoic C8 acid | 80% |
| propionic acid | 20% |
| Mixture 7. | |
| Isononanoic acid (Exxon) | 75% |
| propionic acid | 25% |
| Mixture 8. | |
| Cekanoic C8 acid | 65% |
| Isononanoic acid | 20% |
| propionic acid | 15% |
| Mixture 9. | |
| Cekanoic C8 acid | 60% |
| Isononanoic acid | 21% |
| propionic acid | 19% |

The manganese carboxylate salts of the present invention may be prepared by the process which comprises the steps of
(A) preparing a mixture comprising
(A-1) at least one carboxylic acid characterized by Formula I or a mixture of carboxylic acids comprising at least one carboxylic acid containing at least 6 carbon atoms wherein at least about 75% by weight of the carboxylic acids containing at least 6 carbon atoms in the mixture are characterized by Formula I;
(A-2) manganese metal or a reactive manganese compound; and
(A-3) at least one hydrocarbon solvent; and
(B) maintaining the temperature of the resultant mixture between about 60° C. and below the decomposition temperature of the components and the products for a period of time sufficient to form the manganese salt.

The source of manganese for preparing the manganese salts of the present invention may be manganese metal or a reactive manganese compound such as manganese oxide, manganese nitrate, etc. Manganese oxide (manganous oxide) is a preferred reactive manganese compound in the process of the present invention. The amount of manganese metal or manganese compound added to the mixture prepared in (A) may be any amount although it is generally preferred to add about one equivalent of manganese for each equivalent of carboxylic acid contained in the mixture (A) in order to convert all of the carboxylic acid in the reaction mixture to the manganese salt. Excessive amounts are unnecessary, add to the expense of preparing the salts, and may require removal of unreacted manganese metal or manganese oxide from the desired product.

The mixture prepared in step (A) also contains (A-3) at least one hydrocarbon diluent which is non-reactive with the other components of the mixture, and the diluent may be and preferably is a solvent for the manganese carboxylate salt formed as a product of the process. Examples of hydrocarbon diluents which may be utilized include mineral spirits, mineral oil, synthetic oil or mixtures thereof. The mineral spirits which may be utilized as diluents generally have a boiling range of from about 150° C. to about 215° C. The hydrocarbon diluent used to prepare the mixture (A), may be any aliphatic or aromatic organic solvent which solvates the manganese carboxylate product. The mineral spirits, for example, have been found to be particularly useful in view of their low viscosity, inertness and low cost. Aliphatic solvents which may be used include n-heptane and cyclohexane. Aromatic solvents which may be used include toluene, xylene, cumene and mesitylene.

In one embodiment, it is preferred to include at least one reducing agent in the mixture (A), particularly when the manganese source is manganese oxide. It has been observed that the inclusion of a reducing agent results in a substantial increase in the rate of the reaction. Although not wishing to be bound by any particular theory with regard to the function of the reducing agent, it is believed that the reducing agent reduces any manganese which may be present in its higher positive oxidation state (for example, manganic) to a lower oxidation state (manganous).

Organic or inorganic reducing agents or mixtures of organic and inorganic reducing agents may be used. In one embodiment, a mixture of about equal amounts of an inorganic and an inorganic reducing agent is included in the reaction mixture.

Any reducing agent which is capable of reducing manganese in its higher positive oxidation state to a lower positive oxidation state may be utilized in the process of the present invention. Examples of inorganic reducing agents include metal bisulfites such as sodium bisulfite and various hydrazine sources. The hydrazine source used in the present invention is a compound or mixture of compounds which is capable of producing hydrazine under the conditions of the reaction in sufficient quantity to reduce the manganese oxide from a higher to a lower positive oxidation state. Many such hydrazine sources are known to those of skill in the art. See, for example, the book entitled "Hydrazine" by Charles C. Clark, published by the Mathieson Chemical Corporation of Baltimore, Md. (1953), particularly pp. 31–71 and 120–124 and the book entitled "The Chemistry of Hydrazine" by L. F. Audrieth and B. A. Ogg, published by John Wiley and Son, New York (1951), especially pages 209 through 223. The hydrazine sources are the preferred reducing agents.

Among the more common, and therefore preferred hydrazine sources, are hydrazine itself, hydrazine hydrate and solutions of hydrazine and water, as well as hydrazinium salts of, for example, sulfuric and hydrochloric acid, semicarbazides and thiosemicarbazides and their analogous salts; hydrazine dicarboxylates of lower alkanols (e.g., ROOC-NHNHCOOR) and their dimers as well as the amino guanidines and their —NHNH— sulfuric and hydrochloric acid salts and benzene sulfonyl hydrazides and their bisoxy analogs. Mixtures of hydrazine sources can also be used. This list is not intended to be exhaustive or in any way limit the invention and many useful hydrazine sources similar to those listed will occur to those skilled in the art.

For reasons of economy and ease of handling, hydrazine and particularly its solutions in water and other solvent/diluents are preferred. A typical hydrazine source is a mixture of water and hydrazine containing about 64% hydrazine, although similar mixtures containing more or less hydrazine (about 20–80%; more often, about 30–70% hydrazine) can be used.

Techniques of using such hydrazine sources in chemical reactions are well known to those of skill in the art, as for example is shown by the books cited above and the article entitled "Hydrazine" in Kirk-Othmer Encyclopedia of Chemical Technology, Second Edition, Vol. 11, pp. 164–196, Interscience Publishers, New York, N.Y. (1966). These are hereby incorporated by reference for their relevant disclosures in regard to techniques for using hydrazine sources.

Organic reducing agents which can be included in the reaction mixture (A) include organic aldoximes and ketoximes. In general, oximes of any ketone having from 3 to about 10 carbon atoms, preferably those in which the substituents on the keto-carbon atoms are selected from alkyl groups and saturated alicyclic groups, and oximes of any aldehyde, preferably a saturated aliphatic aldehyde having from 2 to 10 carbon atoms can be used. Examples of oximes are methyl ethyl ketone-oxime, methyl butyl ketone-oxime, 5-methyl-3-heptanone-oxime, cyclohexanone-oxime, and butyraldehyde-oxime.

Oxime agents are commercially available from, for example, Mooney Chemicals, Inc. Skino #1® is butyraldehyde-oxime and Skino #2® is methyl ethyl ketone-oxime.

The amount of reducing agent incorporated into the mixture (A) may be varied over a wide range depending upon the amount of manganese present in the mixture which is at a higher oxidation state. Generally, the amount of reducing agent should be sufficient to reduce all of the manganic ion present to manganous ion. In general, small amounts of the reducing agent are required. For example, from about 0.5 to about 50 parts by weight of a reducing agent may be included in the mixture for every 100 parts of manganese oxide contained in the mixture when the manganese oxide is primarily manganous oxide. Small amounts of reducing agents are included in the mixture (A) when the manganese source is manganese metal in order to reduce any manganic oxide which may be present on the metal.

The reaction mixture also may contain other materials for various ancillary purposes, for example, to serve as dispersing agents or as viscosity modifiers. Examples of viscosity modifiers which are useful in the process of the invention include materials such as glycols, alcohol ethers, glycol ethers, amines and phosphate esters. Some of the ancillary constituents may react and combine with the metal, but the net effect is not deleterious to the process or the ultimate product. For example, alkoxy alkanols of higher molecular weight and boiling ranges may be left in the final product either as a combined organic moiety or merely as a mixture.

Glycols or polyols and glycol ethers often are included as ancillary materials, particularly as viscosity modifiers, and these materials generally fall within the formula

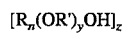 (II)

wherein

R is hydrogen or an alkyl group having from 1 to about 10 carbon atoms, n is 0 or 1, R' is an alkylene group having 2, 3 or 4 carbon atoms which may be substituted with hydroxyl groups, y is an integer from 1 to 4, and z is a value of 2 when n is 0, and a value of 1 when n is 1. The amount of the glycols, polyols or glycol ethers incorporated into the reaction mixture is not critical and can be varied depending on properties desired for the reaction mixture.

Examples of glycols or polyols and glycol ethers represented by the above Formula II include Cellosolve (2-ethoxyethanol); methyl Cellosolve (2-methoxyethanol); Carbitol (diethylene glycol monoethylether); butyl Cellosolve (2-butoxyethanol); diethylene glycol, triethylene glycol, dipropylene glycol, tripropylene glycol, polypropylene glycol, tetraethylene glycol, ethylene glycol and Sorbitol. Mixtures of glycols and glycol ethers can also be used.

Examples of phosphate esters which can be utilized as viscosity modifiers in the reaction mixture include alkyl and aryl phosphates and acid phosphates. Examples of such esters include tributyl phosphate, triamyl phosphate, triphenyl phosphate, tricresyl phosphate, mono amyl acid phosphate, mono butyl acid phosphate, diamyl acid phosphate, dibutyl acid phosphate, and mixtures of one or more of said esters.

The reaction between the manganese and the organic carboxylic acid can occur at room temperature although the rate of the reaction increases with increasing temperature. Accordingly, the mixture of carboxylic acid, diluent and manganese metal or reactive manganese and any optional components described above is maintained at a temperature of from about 20° C. to below the decomposition temperature of the components and the product for a period of time which is sufficient to form the desired manganese salt. Generally, temperatures of from about 100° C. to about 200° C. are utilized to provide a reaction which is completed in a reasonable time. At these temperatures, the reaction is generally completed at from about 3 to about 10 hours. The reaction preferably is conducted with bubbling or purging using an inert gas such as nitrogen gas. Elevated pressures can be utilized in the process of the present invention, but the process generally is conducted at about atmospheric pressure.

As noted above, the process of the present invention involves preparing a mixture of the carboxylic acid, manganese metal or a reactive manganese salt and a diluent. In one embodiment, a mixture of the carboxylic acid and a diluent is first prepared and heated to a temperature such as about 60°–100° C., and the manganese metal or reactive manganese compound is then added to the mixture followed by heating at the higher temperatures to complete the reaction. The optional components such as the reducing agents may be included in the initial mixture or added to the mixture subsequent to the addition of the manganese metal or manganese oxide. In a preferred embodiment, a mixture of the carboxylic acid, reducing agent and diluent is prepared, heated to a temperature of about 60°–80° C., and manganese oxide is then added while the mixture is sparged with nitrogen. After the addition of the manganese oxide, the mixture is heated to a temperature of about 130°–150° C. in an atmosphere of inert gas to complete the reaction. At the end of the reaction, a viscosity modifier such as one of the phosphate esters described above may be added to the diluted reaction product of the mixture prior to cooling.

The manganese carboxylate salts prepared in accordance with the method of this invention are hydrocarbon-soluble and water-insoluble. The manganese carboxylate salts prepared from carboxylic acids represented by Formula I and prepared in accordance with the method described above are characterized as having a color which is lighter than manganese carboxylate salts prepared from carboxylic acids which are not characterized by Formula I. That is, solutions of manganese salts prepared from carboxylic acids wherein the α- or 2-carbon atom contains one or two substituents (e.g., 2-ethylhexanoic acid and neodecanoic acid) dissolved in solvents such as mineral spirits are characterized by a much darker color than mineral spirit solutions of the manganese salts of the present invention. The colors of the solutions are rated using the Gardner Color Scale.

The following examples illustrate the process of the present invention for preparing the manganese carboxylate salts of the invention. Unless otherwise indicated in the following examples and elsewhere in the specification and appended claims, all parts and percentages are by weight, all temperatures are in degrees Centigrade, and pressure is at or near atmospheric pressure.

Example 1

A mixture of 109.7 parts of propionic acid, 346.3 parts of Cekanoic C8 acid, 121.2 parts of isononanoic acid (Exxon), 277 parts of mineral spirits, 100 parts of butyl Cellosolve, 6 parts of hydrazine hydrate and 6 parts of methylethyl ketone-oxime (Skino #2) is prepared and sparged with nitrogen as the mixture is heated to about 65° C. whereupon 158 parts of manganese oxide are added. The mixture is then heated to about 95° C. over a period of 5 hours and then to a temperature of about 140° C. over a period of about 3 hours. At this time 100 parts of butyl acid phosphate are added and the mixture is maintained at about 140° C. for an additional 5 minutes. The mixture is cooled and filtered. The filtrate is the desired product. When a portion of the filtrate is diluted to 12% manganese with mineral spirits, the diluted solution has a color rating of 13–14 on the Gardner Color Scale.

Example 2

A mixture of 82 parts of propionic acid, 380.5 parts of Cekanoic C8 acid, 119.6 parts of isononanoic acid (Exxon), 100 pans of butyl Cellosolve, 277 pans of mineral spirits, 4 parts of hydrazine hydrate and 4 parts of methylethyl ketone-oxime is prepared, and the mixture is sparged with nitrogen as it is heated to about 60° C. To this mixture there is added 165 parts of manganese oxide, and the mixture is heated to a temperature of about 100° C. over a period of 2 hours and thereafter to a temperature of about 145° C. over 2 hours. At this temperature, 100 parts of butyl acid phosphate are added and the mixture is heated to about 160° C. for 1 hour. After cooling, the mixture is filtered, and the filtrate is the desired product. A portion of the filtrate is diluted to 12.0% manganese with mineral spirits, and the diluted solution has a color rating of 13 on the Gardner Color Scale.

The hydrocarbon-soluble manganese salts of the present invention are useful in a variety of applications including lubricants, fuels, resins, inks and paints, particularly in inks and paints.

The manganese salt compositions of this invention are useful as additives for paint formulations comprising pigments and vehicle as well as pigment extenders and pigment suspending agents which generally are considered as part of the pigment. Binders, thinners, driers, as well as other optional ingredients such as anti-skin, and anti-slip agents generally are considered in the art as part of the vehicle. The paints to which the manganese salts of the present invention can be added can be of the primer, enameled, glossy, semi-glossy or flat type. Examples of suitable pigments for the paint formulations include the inorganic and organic types well known in the art such as red iron oxide, zinc oxide, zinc chromate, titanium dioxide, lithopone, carbon black, and prussian blue.

Examples of pigment extenders which can be utilized include calcium carbonate, magnesium silicate, silica, aluminum silicate, asbestine, talc, barytes, gypsum, clay or chalk. Exemplary pigment suspending agents include aluminum stearate and zinc stearate.

Binders which can be employed in paints include the vegetable oils such as linseed, both boiled and raw, soybean, tung oil, synthetic polyester-type oils such as glycerine, erythritol or pentaerythritol esters of fatty acids or phthalic acid and their anhydrides, phenolic resins and alkyl alkyd solids. Examples of suitable thinners include mineral spirits (boiling range 150°–15° C.), turpentine and petroleum naphtha. Optional driers which can be utilized include the naphthenates, oxides, resinates, oleates and acetates of cobalt, manganese, lead and zinc. The preferred driers are the naphthenates of cobalt, manganese and lead.

Paint formulations containing the manganese salts of the invention can be prepared by methods well known in the art. For example, the pigment and vehicle of the paint can be mixed followed by the addition of the manganese salts of the invention and other optional additives. Alternatively, the vehicle and manganese salt can be mixed followed by the addition of pigment and other optional ingredients.

The manganese salt compositions of the present invention function primarily as driers, and, therefore, an amount which is effective to provide the desired drying characteristics of the paint is the amount normally included in the paint formulation. Accordingly, the amount of manganese salt incorporated into the paint formulation can range from as little as 0.01% to about 5% to 10% . Generally, however, the paint formulation will contain less than 2% by weight of the manganese salt.

The manganese salt compositions of the present invention also are useful for reducing the drying time of ink formulations. Ink formulations also are generally comprised of a pigment and a vehicle, and other optional ingredients to alter and improve the properties of the ink formulation. The nature of the vehicle selected will be determined by the properties desired including the properties desired of the dried ink formulation. Examples of vehicles which can be utilized in inks include paraffinic hydrocarbons, drier oils such as linseed oil, tung oil and soya oil, and synthetic, polymeric vehicles such as alkyd resins and oil-modified alkyd resins. Examples of pigments which can be utilized include polyvalent metal compounds such as nickel carbonate and copper hydroxide. Examples of suitable thinners include mineral spirits, turpentine and petroleum naphtha. Other optional ingredients which can be included in the ink formulations include anti-skinning and anti-slipping agents.

The amount of manganese salt compositions of the present invention included in the ink formulations of the invention will be an amount which is effective to reduce the drying time of said ink. Generally, the amount of manganese salt included in the ink will range from about 0.1% to about 5% by weight, but the amount most often will be less than 3% by weight of the ink formulation.

The manganese salts prepared in accordance with the process of the present invention also are useful as accelerators in the curing of unsaturated polyester resin compositions. The unsaturated polyester resin compositions which can be accelerated with the manganese salts of the present invention are solutions of unsaturated polyester resins and a polymerizable monomer which provides cross-linking units to unite the polymer chains. The polyester and monomer copolymerize upon the introduction of a catalyst such as a peroxide catalyst to form a rigid, insoluble, infusible material. The unsaturated polyester resin compositions are used in the production of coatings, laminates, cast articles, molded articles, and other shaped articles.

Accelerators are usually added to unsaturated polyester resin compositions to accelerate the decomposition of the peroxide catalyst to free radicals and thereby initiate or speed up the curing of the composition at relatively low temperatures, i.e., at temperatures in the range of −30° C. to +30° C. The manganese salts of the present invention, are effective accelerators, and can be used alone, or in combination with other known accelerators such as vanadium, cobalt, iron, and aluminum salts of organic acids; amines such as dimethyl aniline, diethyl aniline, and 2-aminopyridene; Lewis acids, such as boron fluoride dihydrate, and ferric chloride; bases such as tetraethyl ammonium hydroxide and tetramethyl ammonium hydroxide, etc. Cobalt salts of organic acids are the most widely used accelerators for the low temperature decomposition of peroxide catalysts and in the curing of unsaturated polyester resin compositions.

The polyester resins that are used in the practice of this invention are unsaturated polyester resins that are formed by condensing an unsaturated polycarboxylic acid or anhydride with at least one polyhydric alcohol. Illustrative of these polyester resins are the products of the reaction of a dicarboxylic acid or anhydride, such as phthalic anhydride, isophthalic acid, tetrahydrophthalic anhydride, hexahydrophthalic anhydride, tetrachlorophthalic anhydride, hexachloroendomethylene tetrahydrophthalic acid, succinic acid, glutaric acid, adipic acid, pimelic acid, suberic acid, azelaic acid, and sebacic acid, and/or an unsaturated dicarboxylic acid or anhydride, such as maleic anhydride, fumaric acid, chloromaleic acid, itaconic acid, citraconic acid, and mesaconic acid, with a dihydric alcohol, such as ethylene glycol, propylene glycol, butylene glycol, diethylene glycol, triethylene glycol, and neopentyl glycol. Small amounts of a polyhydric alcohol, such as glycerol, pentaerythritol, trimethylolpropane, or sorbitol, may be used in combination with the glycol.

A three-dimensional structure is produced by reacting the unsaturated polyester through the unsaturated acid component with an unsaturated monomer that is capable of reacting with the polyester resin to form cross-linkages. Suitable unsaturated monomers include styrene, methylstyrene, dimethylstyrene, vinyltoluene, divinylbenzene, dichlorostyrene, methyl acrylate, ethyl acrylate, methyl methacrylate, ethyl methacrylate, diallyl phthalate, vinyl acetate, triallyl cyanurate, acrylonitrile, acrylamide, and mixtures thereof. The relative amounts of the unsaturated polyester resin and the unsaturated monomer in the composition may be varied over a wide range. In order to prevent gelation during manufacture and storage, the polyester resin may be stabilized as known in the art. Some examples of well-known stabilizers include hydroquinone, quinone, tertiary butyl catechol, etc.

The unsaturated polyester resin compositions generally contain 20% to 80% by weight of the monomer, with the monomer content preferably in the range of 30% to 70% by weight.

When it is desired to copolymerize the unsaturated polyesters with the unsaturated monomer to form a useful solid product, some source of free radicals is added. The free radicals cause copolymerization of the monomer and polyester to yield a cross-linked material whose properties are dependent on the original choice of dicarboxylic acids, polyhydric alcohols, and unsaturated monomers. Typical free radical producing catalysts include the various redox systems, high-energy electron beams, and a variety of peroxide compounds.

An organic peroxide that decomposes to release free radicals at temperatures in the range of 0° to 30° C. generally is used to catalyze the copolymerization reaction between the unsaturated polyester resin and the unsaturated monomer. Among the peroxide catalysts that can be used are methyl ethyl ketone peroxide, benzoyl peroxide, cumene hydroperoxide, cetyl peroxide, lauryl peroxide, cyclohexanone peroxide, 2,4-dichlorobenzoyl peroxide, bis(p-bromobenzoyl)peroxide, acetyl peroxide, and di-tert-butyl diperphthalate. The peroxide catalysts that are most commonly used are methyl ethyl ketone peroxide, benzoyl peroxide, and cumene hydroperoxide. The amount of peroxide catalyst used is from 0.1% to 2.0% and preferably from 0.6% to 1.0% of the weight of the unsaturated polyester resin composition.

The amount of the manganese salt of the invention included in the 25 polyester resin formulation is an amount which is effective to accelerate the decomposition of the peroxide and to reduce the drying (or gel time) of the resin formulation. Generally, the amount of accelerator will be sufficient to provide from about 0.0001% to 1.0% of manganese (as metal). More typically the range will be about 0.001% to about 0.1% . When more than one accelerator is used, the total amount of metal will fall within this range. For example, the manganese salts of the invention can be used in combination with other metal salts normally used as accelerators for polyester resins. Such salts include cobalt, manganese, iron, and aluminum salts prepared by methods known to those skilled in the art.

In addition to the unsaturated polyester resin, cross-linking monomer, peroxide catalyst, and one of the accelerator systems of this invention, the unsaturated polyester resin compositions may also contain an inhibitor, such as tert-butyl catechol or hydroquinone, fillers and pigments, dyes, mold release agents, plasticizers, stabilizers, flame retardants, and other additives in the amounts ordinarily used for these purposes.

The unsaturated polyester resin compositions that comprise an unsaturated polyester resin, an unsaturated monomer, a peroxide catalyst, and a manganese salt accelerator system cure rapidly without application of heat to form rigid, insoluble, and infusible products.

The manganese carboxylate salts also are useful in improving the properties of lubricants and fuels. Lubricating compositions may be formulated for a variety of uses, and the lubricating compositions are based on diverse oils of lubricating viscosity, including natural and synthetic lubricating oils and mixtures thereof. The lubricating compositions which contain the manganese carboxylate salts of the present invention can be used as crankcase lubricating oils for spark-ignited and compression-ignited internal combustion engines, as automatic transmission fluids, gear lubricants, metal-working lubricants, hydraulic fluids, etc. The amount of the manganese salt included in the lubricating compositions is sufficient to provide the lubricating compositions with improved properties. Normally, the amount employed will be from about 0.01% to about 20% , preferably about 0.1% to about 10% by weight of the total weight of the lubricating compositions. The lubricating compositions may include other well-known additives normally used in lubricating compositions such as, for example, detergents and dispersants, corrosion- and oxidation-inhibiting agents, pour point depressing agents, extreme pressure agents, anti-wear agents, color stabilizers and anti-foam agents.

The fuel compositions containing the manganese carboxylate salts of the present invention contain a major proportion of a normally liquid fuel, usually a hydrocarbonaceous petroleum distillate fuel such as motor gasoline as defined by ASTM Specification D-439 and diesel fuel or fuel oil as defined by ASTM Specification D-396. Generally these fuel compositions contain a property-improving amount of the manganese carboxylate salts of the present invention. Usually, this amount is from about 1 to about 50,000 parts by weight, preferably about 4 to about 5,000 parts by weight of the manganese carboxylate salts of the present invention per million parts of fuel. The fuel compositions can contain, in addition to the manganese carboxylate salts of this invention, other additives which are well known to those skilled in the art. Such additives include anti-knock agents, lead scavengers, deposit preventers or modifiers, anti-oxidants, rust inhibitors, bacteriostatic agents, gum inhibitors, metal deactivators, demulsifiers, etc.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

I claim:

1. A manganese carboxylate salt derived from (a) at least one carboxylic acid containing at least about six carbon atoms and characterized by the Formula (I)

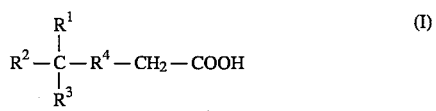

wherein $R^1$, $R^2$ and $R^3$ are each independently hydrogen or alkyl groups, and $R^4$ is an aliphatic hydrocarbylene group, provided that when $R^1$ and $R^2$ are hydrogen, $R^4$ is a branched aliphatic hydrocarbylene group, or (b) a carboxylic acid mixture comprising at least one carboxylic acid containing at least about 6 carbon atoms wherein at least about 75% by weight of the carboxylic acids containing at least 6 carbon atoms in the mixture are characterized by Formula I.

2. The manganese carboxylate salt of claim 1 wherein the carboxylic acids of Formula I contain from about 6 to about 30 carbon atoms.

3. The manganese carboxylate salt of claim 1 wherein the carboxylic acids of Formula I contain from about 6 to about 15 carbon atoms.

4. The manganese carboxylate salt of claim 1 wherein $R^4$ is a branched hydrocarbylene group.

5. The manganese carboxylate salt of claim 1 derived from (a) a mixture of carboxylic acids of Formula I containing at least about 40% by weight of carboxylic acids wherein $R^1$ and $R^2$ are alkyl groups containing 1 to about 4 carbon atoms and $R^3$ is either hydrogen or an alkyl group.

6. The manganese carboxylate of claim 5 wherein $R^1$ and $R^2$ are methyl groups and $R^3$ is hydrogen or a methyl group.

7. The manganese carboxylate salt of claim 1 derived from (b) a carboxylic acid mixture of (i) carboxylic acids containing at least 6 carbon atoms wherein at least about 75% by weight of the carboxylic acids containing at least 6 carbon atoms are characterized by Formula I, and (ii) at least one aliphatic carboxylic acid containing from 1 to 4 carbon atoms.

8. The manganese carboxylate salt of claim 1 derived from a carboxylic acid mixture which comprises (i) from about 75% to about 95% by weight of a mixture of carboxylic acids wherein at least about 80% by weight of the carboxylic acids containing at least about 6 carbon atoms are characterized by Formula I, and (ii) from about 5% to about 25% by weight of at least one carboxylic acid containing from 2 to 4 carbon atoms.

9. The manganese carboxylate salt of claim 8 wherein the carboxylic acid containing from 2 to 4 carbon atoms is propionic acid.

10. The manganese carboxylate salt of claim 1 wherein the carboxylic acid of Formula I is selected from 3,5-dimethylhexanoic acid, 4,5-dimethylhexanoic acid, 3,5,5-trimethylhexanoic acid, and mixtures thereof.

11. A hydrocarbon soluble manganese carboxylate salt derived from a carboxylic acid mixture comprising (i) from about 75% to about 95% by weight of at least one carboxylic acid containing from 6 to about 15 carbon atoms wherein at least about 80% by weight of said acids are characterized by Formula I.

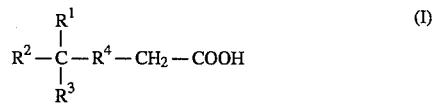

wherein $R^1$, $R^2$ and $R^3$ are each independently hydrogen, methyl or ethyl groups and $R^4$ is a hydrocarbylene group, and (ii) from about 5 to about 25% of propionic acid.

12. The manganese carboxylate salt of claim 11 wherein $R^1$ and $R^2$ are methyl groups, $R^3$ is hydrogen or a methyl group, and $R^4$ is a branched hydrocarbylene group.

13. The manganese carboxylate salt of claim 11 wherein at least about 85% of the acids containing from 6 to 15 carbon atoms are characterized by Formula I.

14. The manganese carboxylate salt of claim 11 wherein at least one carboxylic acid (i) is selected from 3,5-dimethylhexanoic acid, 4,5-dimethylhexanoic acid, 3,5,5-trimethylhexanoic acid, and mixtures thereof.

15. A method for preparing a hydrocarbon-soluble manganese salt of (a) at least one organic carboxylic acid containing at least 6 carbon atoms and characterized by the Formula (I)

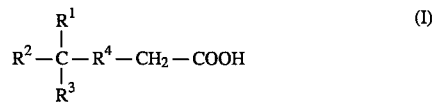

wherein $R^1$, $R^2$ and $R^3$ are each independently hydrogen or alkyl groups, and $R^4$ is a hydrocarbylene group, or (b) a carboxylic acid mixture comprising at least one carboxylic acid containing at least 6 carbon atoms wherein at least about 75% by weight of the acids containing at least 6 carbon atoms are characterized by Formula I which comprises the steps of (A) preparing a mixture comprising
  (A-1) at least one carboxylic acid characterized by Formula I or a mixture of carboxylic acids comprising at least one carboxylic acid containing at least 6 carbon atoms wherein at least about 75% by weight of the carboxylic acids containing at least 6 carbon atoms in the mixture are characterized by Formula I,
  (A-2) manganese metal or a reactive manganese compound, and
  (A-3) at least one hydrocarbon diluent.

(B) maintaining the temperature of the resultant mixture between about 20° C. and below the decomposition temperature of the components and product for a period of time sufficient to form the manganese salt.

16. The method of claim 15 wherein manganese oxide is included in the mixture prepared in (A).

17. The method of claim 15 wherein the mixture prepared in (A) also contains (A-4) at least one reducing agent.

18. The method of claim 17 wherein the reducing agent is a hydrazine source.

19. The method of claim 15 wherein the acids of Formula I contain from about 6 to about 15 carbon atoms.

20. The method of claim 15 wherein the mixture prepared in (A) also comprises at least one aliphatic carboxylic acid containing from 2 to about 4 carbon atoms.

21. The method of claim 20 wherein the acid containing 2 to 4 carbon atoms is propionic acid.

22. The method of claim 15 wherein the mixture prepared in (A) comprises a mixture of acids of Formula I containing at least about 40% by weight of carboxylic acids wherein $R^1$ and $R^2$ are methyl groups, $R^3$ is hydrogen or methyl group, and $R^4$ is a branched hydrocarbylene group.

23. The method of claim 15 wherein the mixture of (A) is prepared by adding the manganese metal or reactive manganese compound to a mixture of the carboxylic acid and the diluent.

* * * * *